United States Patent
Hawthorne et al.

(10) Patent No.: US 6,664,426 B1
(45) Date of Patent: Dec. 16, 2003

(54) ETHER AND ESTER DERIVATIVES OF THE PERBORATE ICOSAHEDRON

(75) Inventors: M. Frederick Hawthorne, Encino, CA (US); Toralf Peymann, Munich (DE); Andreas Maderna, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/592,214

(22) Filed: Jun. 12, 2000

Related U.S. Application Data (63) Continuation-in-part of application No. 09/546,108, filed on Apr. 10, 2000, now Pat. No. 6,323,372.

(51) Int. Cl.$^7$ .................................................. C07F 5/02
(52) U.S. Cl. ............................... 568/5; 568/4; 423/276
(58) Field of Search ........................... 568/4, 5; 423/276

(56) References Cited

U.S. PATENT DOCUMENTS 5,489,673 A * 2/1996 Wilbur ...................... 536/17.1
5,714,591 A * 2/1998 Yamamoto et al. ........... 534/16

OTHER PUBLICATIONS

CA:135:137535 abs of Angewandte Chemie, International Edition by Peymann et al 40(9) pp 1664–1667 2001.*

CA:121:220130 abs of Koordinatsionnaya Khimiya by Kuzentsov et al 20(6) pp 429–430 1994.*

CA:128:308516 abs of Tetrahedron by Ghaneolhosseine et al 54(15) pp 3877–3884 1998.*

* cited by examiner

*Primary Examiner*—Jean F. Vollano
(74) *Attorney, Agent, or Firm*—Koppel, Jacobs, Patrick & Heyrl; Michael J. Ram

(57) ABSTRACT

New boron icosahedral ethers and esters formed from $Cs_2[closo-B_{12}(OH)_{12}]$,; $Cs[closo-1-H-1-CB_{11}(OH)_{11}]$; and $closo-1,12-H_2-1,12-C_2B_{10}(OH)_{10}$ are disclosed. Also set forth are their preparation by reacting the icosahedral boranes $[closo-B_{12}H_{12}]^{2-}$, $[closo-1-CB_{11}H_{12}]^-$ and $closo-1,12-(CH_2OH)_2-1,12-C_2B_{10}H_{10}$ with an acid anhdride or acid chloride to form the ester or an alkylating agent to form the ether.

5 Claims, 8 Drawing Sheets

ETHER AND ESTER DERIVATIVES OF THE PERBORATE ICOSAHEDRON

This is a Continuation-in-Part of Ser. No. 09/546108 filed Apr. 10, 2000, now U.S. Pat. No. 6,323,372.

The present invention relates to unique three-dimensional ester and ether icosahedral boron cage compounds. This invention was made with Government support under Contract No. DF-FG03-95ERG1975 awarded by the Department of Energy. The Government has certain rights in this invention.

BACKGROUND

Scientists have formed numerous different polyhydroxylated molecules. Carbon-based systems are well-known. For example, carbohydrates are ubiquitous in nature and serve as a source for chemical energy (glucose), the backbone for genetic information (ribose), and the organic constituents of plants (cellulose) or insects (chitin) (D. Voet, J. G. Voet, *Biochemistry*, 2nd ed., Wiley, New York, 1995, pp. 251–276. The three-dimensional network of silica and its derived minerals (F. Liebau, *Structural Chemistry of Silicates*, Springer, New York, 1985, p. 4) results from the condensation of polyhydroxylated silicates.

However, very few polyhydroxylated boron compounds are known. The most prominent polyhydroxylated boron compound is boric acid, $B(OH)_3$. Alkaline solutions of $B(OH)_3$ deposit $Na_2[B_4O_5(OH)_4]\cdot nH_2O$, which constitutes two abundant boron minerals, kernite (n=2) and borax (n=8) (F. A. Cotton, G. Wilkinson, *Advanced Inorganic Chemistry*, 5th ed., Wiley, New York, 1988, pp. 164–169.). Other common boron structures include the trigonal and tetrahedral boron-oxygen units common to borate minerals, (G. A. Heller, *Top. Curr. Chem.* 1986, 131, 39–98), and the icosahedron. The allotropes of elemental boron, (J. Donohue, *The Structures of the Elements*, Wiley, New York, 1974, pp. 48–82) boron-rich solids (H. Hubert, B. Devouard, L. A. J. Garvie, M. O'Keeffe, P. R. Buseck, W. T. Petuskey, P. F. McMillan, *Nature* 1998, 391, 376–378) and the parent anion of the polyhedral boranes, $[closo-B_{12}H_{12}]^{2-}$ First reported by Hawthorne et al (A. R. Pitochalli and M. F. Hawthorne *J. Am.Chem. Soc.*, 1960, 82, 3228 followed by J. A. Wunderlich, W. N. Lipscomb, *J. Am. Chem. Soc.* 1960, 82, 4427–4428) all contain $B_{12}$ icosahedral The charge-delocalized icosahedral ion $[closo-B_{12}H_{12}]^{2-}$, may be considered as the parent aromatic species for borane chemistry in a manner similar to that served by the benzene ring in organic (carbon) chemistry (M. F. Hawthorne, *Advances in Boron Chemistry*, Special Publication No. 201, Royal Society of Chemistry, London, 1997, pp. 261–272). However, while certain benzene and other aromatic compounds are known,(ie., phenol, hydroquinone, naphthol) fully hydroxylated aromatic compounds (all —H replaced by —OH) are not known or readily prepared. However, contrary to the process described herein for manufacturing the new hydoxylated borates, no reaction occurs when benzene is refluxed with boiling hydrogen peroxide. Isoelectronic substitution of one or two :B—H vertices in $[closo-B_{12}H_{12}]^{2-}$ by :C—H$^+$ provides the aromatic derivatives $[closo-1-CB_{11}H_{12}]^-$, and a set of three isomeric dicarbacarboranes (1,2- or ortho; 1,7- or meta; and 1,12- or para) $closo-C_2B_{10}H_{12}$ R (N. Grimes, *Carboranes*, Academic Press, New York, 1970, p. 8). Each of these isoelectronic derivatives of $[closo-B_{12}H_{12}]^{2-}$, undergoes characteristic hydrogen-substitution reactions at their B—H vertices resulting in a huge number of known icosahedral species.

Of special interest are derivatives in which every available B—H vertex has been substituted. Thus, hydrophobic derivatives of $[closo-B_{12}H_{12}]^{2-}$ and $[closo-1-CB_{11}H_{12}]^-$, and the three isomeric dicarboboranes, such as $[closo-B_{12}Cl_{12}]^{2-}$ (W. H. Knoth, H. C. Miller, J. C. Sauer, J. H. Balthis, Y. T. Chia, E. L. Muetterties, *Inorg. Chem*, 1964, 3, 159–167), $[closo-CB_{11}(CH_3)_{12}]^-$, (King, B. T.; Janousek, Z.; Grüner, B.; Trammell, M.; Noll, B. C.; Michl, J. *J Am. Chem. Soc.* 1996, 118, 10902–10903), $closo-1,12-C_2B_{10}(CH_3)_{12}$, (W. Jiang, C. B. Knobler, M. D. Mortimer, M. F. Hawthorne, *Angew. Chem.* 1995, 107, 1470–1473; *Angew. Chem. Int. Ed. Engl.* 1995, 34, 1332–1334.) and, $[closo-B_{12}(CH_3)_{12}]^{2-}$ (T. Peymann, C. B. Knobler, M. F. Hawthorne, *J.Am. Chem. Soc.*, 1999, 121, 5601) have been synthesized. However, the existence or formulation of similar highly substituted polyhedral borane derivatives having hydrophilic substituents, such as hydroxyl have not been demonstrated.

It was found that per-B-hydroxylated icosahedral borane derivatives, which may be considered to be derivatives of a new type of polyhedral sub-boric acid, can be readily synthesized. Described herein are the per-B-hydroxylated icosahedral $Cs_2[closo-B_{12}(OH)_{12}]$,; $Cs[closo-1-H-1-CB_{11}(OH)_{11}]$; and $closo-1,12-H_2-1,12-C_2B_{10}(OH)_{10}$. These borohydrate compounds are prepared by the oxidation of the icosahedral boranes $[closo-B_{12}H_{12}]^{2-}$, $[closo-1-CB_{11}H_{12}]^-$ and $closo-1,12-(CH_2OH)_2-1,12-C_2B_{10}H_{10}$, respectively, with 30%$_W$ hydrogen peroxide at the reflux temperature (from about 100° C. to 50° C.) (Peymann T. etal, *Angew, Chem. Ind. Ed*, 1999, 38, No.8, 1062–1063)

SUMMARY

It has now been found that all of the hydroxyls on per-B-hydroxylated icosahedral boranes can be readily converted to ethers and esters with the general formulas $[closo-B_{12}(OCOR)_{12}]^{2-}$ and $[closo-B_{12}(OCR)_{12}]^{2-}$ where R is an alkyl, alkene or alkyne or a benzyl or substituted benzyl group. The esters are prepared by reacting the perhydroxylated compound with an organic anhydride or acid chloride, such as acetic anhydride or benzoyl chloride. The ether is prepared by reacting the perhydroxylated compound with various alkylating agents such as benzyl chloride.

DRAWINGS

These and other features, aspects and advantages of the present invention will become better understood with reference to the following description, appended claims, and accompanying drawings, where:

Figure 3:
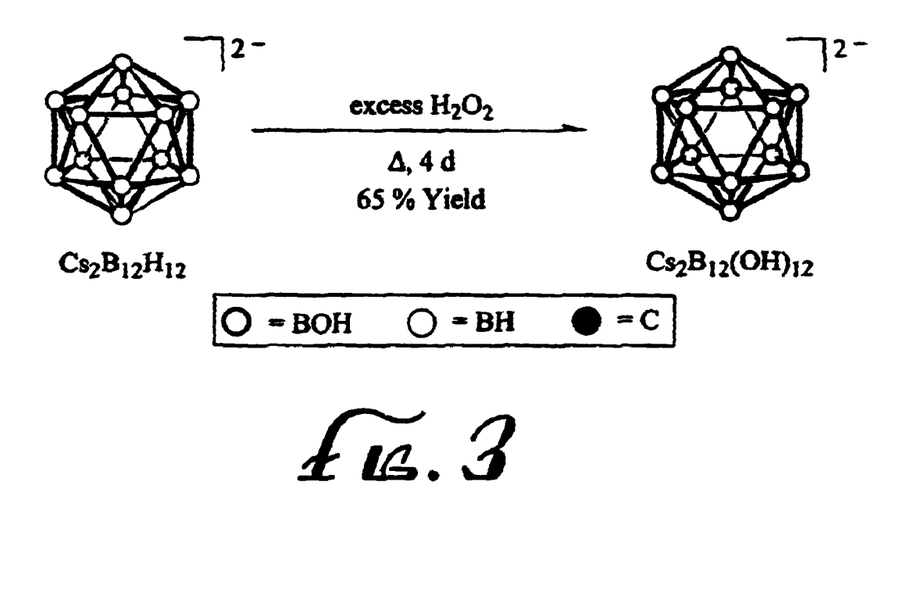
FIG. 3 shows the reaction scheme for formation of $Cs_2[closo-B_{12}(OH)_{12}]$.
Figure 4:
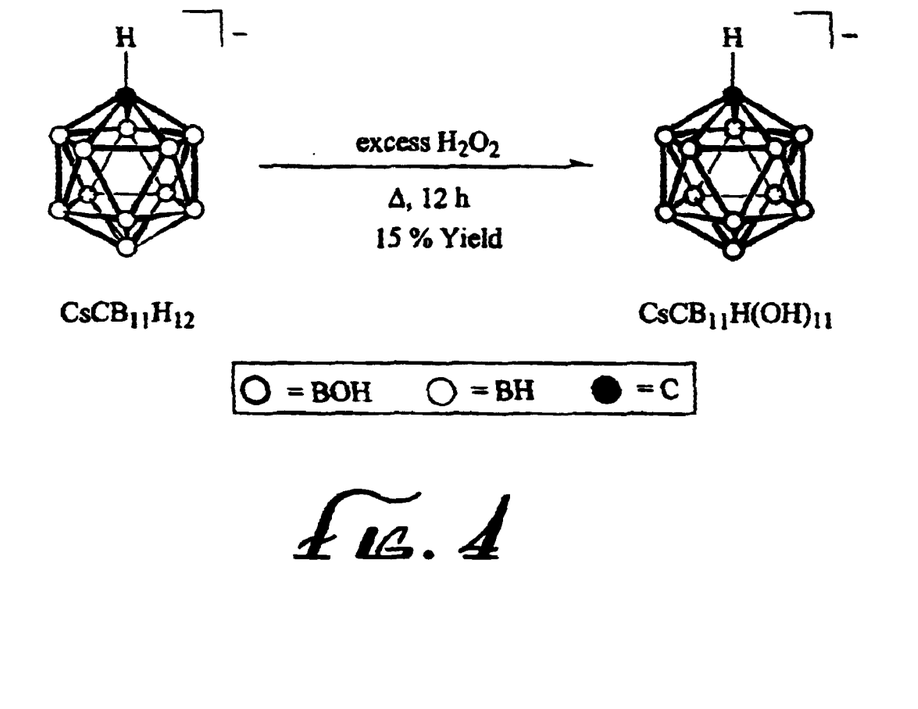
FIG. 4 shows the reaction scheme for formation of $Cs[closo-1-H-1-CB_{11}(OH)_{11}]$.
Figure 5:
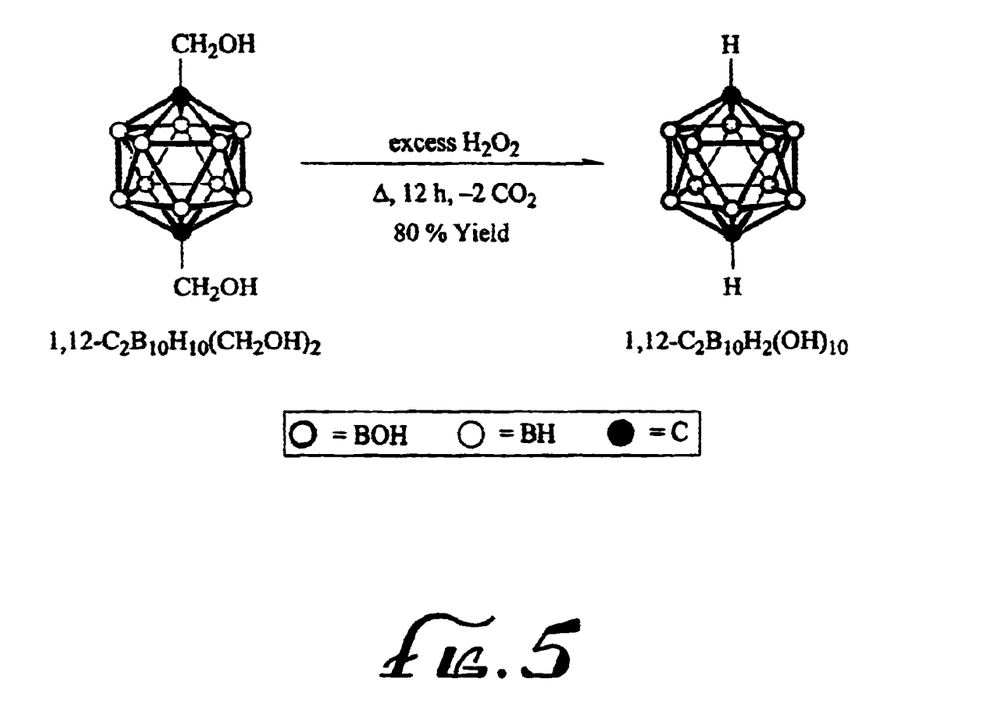
FIG. 5 shows the reaction scheme for formation of $closo-1,12-H_2-1,12-C_2B_{10}(OH)_{10}$.

DETAILED DESCRIPTION $Cs_2[closo-B_{12}(OH)_{12}]$, $Cs[closo-1-H-1-CB_{11}(OH)_{11}]$, and $closo-1,12-H_2-1,12-C_2B_{10}(OH)_{10}$ are prepared by refluxing between 100° C. and 150° C., the icosahedral boranes $[closo-B_{12}H_{12}]^{2-}$, $[closo-1-CB_{11}H_{12}]^-$ and $closo-1,12-(CH_2OH)_2-1,12-C_2B_{10}H_{10}$, respectively, as shown in FIGS. 3–5, with 30% (by volume) hydrogen peroxide. While 30% (by weight, $\%_W$) hydrogen perioxide boils at 222° F. (106° C.) and 100% hydrogen peroxide boils at about 150° C., the reflux temperature in the reactions will depend on the specific boron compound utilized, its concentration in the reaction mixture and the extent of reaction. As shown in FIGS. 3–5, the borane was refluxed for 4 days and the carboranes were refluxed for 15 hours.

Figure 1:
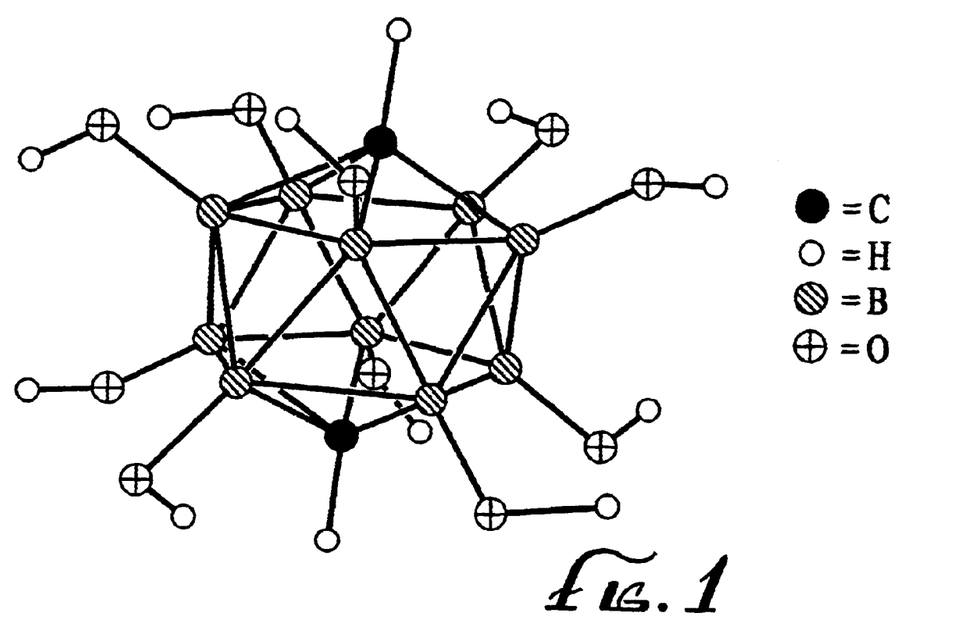
FIG. 1 is an ORTEP diagram of $closo-1,12-H_2-1,12-C_2B_{10}(OH)_{10}$.
Figure 2:
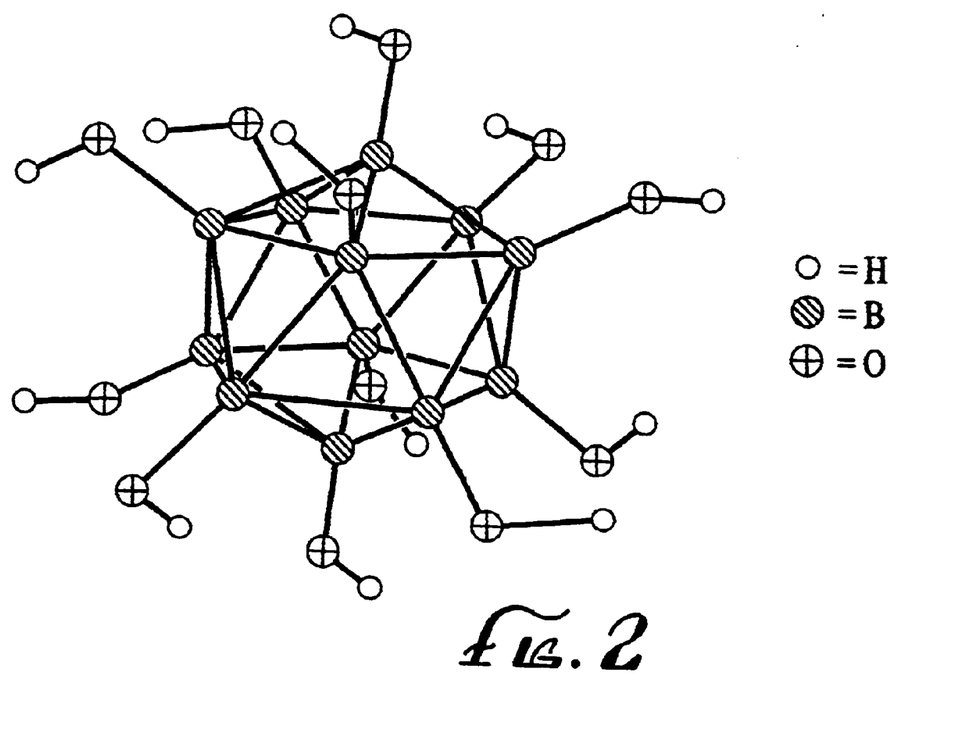
FIG. 2 is an ORTEP diagram of $Cs_2[closo-B_{12}(OH)_{12}]$.

$Cs_2[closo-B_{12}(OH)_{12}]$ is shown in FIG. 1 and $closo-1,12-H_2-1,12-C_2B_{10}(OH)_{10}$ is shown in FIG. 2. The sparingly water-soluble salts $Cs_2[closo-B_{12}H_{12}]^{2-}$ and $Cs[closo-1-CB_{11}H_{12}]^-$, served as precursors for $Cs_2[closo-B_{12}(OH)_{12}]$ and $Cs[closo-1-H-1-CB_{11}(OH)_{11}]$, respectively. The synthesis of $closo-1,12-H_2-1,12-C_2B_{10}(OH)_{10}$ employed the slightly water-soluble precursor $closo-1,12-(CH_2OH)_2-1,12-C_2B_{10}H_{10}$, because $closo-1,12-C_2B_{10}H_{12}$ is not water-soluble and hence not available to the hydrogen peroxide reagent. During this reaction sequence, the diol $closo-1,12-(CH_2OH)_2-1,12-C_2B_{10}H_{10}$, is most likely oxidized to the corresponding dicarboxylic acid, which subsequently decarboxylates during B-hydroxylation to afford species $closo-1,12-H_2-1,12-C_2B_{10}(OH)_{10}$.

The yields from the syntheses shown in FIGS. 3–5 are 80% for $closo-1,12-H_2-1,12-C_2B_{10}(OH)_{10}$, 65% for $Cs_2[closo-B_{12}(OH)_{12}]$ and 31% for $Cs[closo-1-H-1-CB_{11}(OH)_{11}]$. This distribution reflects the higher kinetic stabilities of the two centrosymmetric cage structures of $[closo-B_{12}H_{12}]^{2-}$ and $closo-1,12-C_2B_{10}H_{10}$ relative to that of the polarized cluster $[closo-1-CB_{11}H_{12}]^-$.

The alkali-metal salts of the $Cs_2[closo-B_{12}(OH)_{12}]$ have a low solubility in water even though its surface is covered with hydroxyl groups. Therefore, $Cs_2[closo-B_{12}(OH)_{12}]$ can be recrystallized from water, whereas the $Li_2$, $Na_2$, and $K_2$ salts of $Cs_2[closo-B_{12}(OH)_{12}]$ precipitate quantitatively upon addition of the corresponding alkali-metal chloride to warm aqueous solutions of $Cs_2[closo-B_{12}(OH)_{12}]$. The dicesium salt is freely soluble in water since cesium is to large to effectively coordinate to the $[B_{12}(OH)_{12}]^{2-}$ ion.

The ability to produce $Cs_2[closo-B_{12}(OH)_{12}]$, $Cs[closo-1-H-1-CB_{11}(OH)_{11}]$ and $closo-1,12-H_2-1,12-C_2B_{10}(OH)_{10}$, opened up a new field of boron cluster chemistry, wherein the aromatic icosahedral cluster functions as the scaffolding for reactions that would be performed on its oxygen sheathing. For example, $Cs_2[closo-B_{12}(OH)_{12}]$ can be used as the central core for the formation of multioligomeric organic and inorganic compounds similar to dendrimers (G. R. Newkome, C. N. Moorefield, F. Vögtle, *Dendritic Molecules*, VCH, New York, 1996). except that the oligomeric chains will emanate from a molecular surface rather than a single atoms. Furthermore, it is believed that the high temperature pyrolysis of a simple salt of $Cs_2[closo-B_{12}(OH)_{12}]$, might form a polymeric network of very stable icosahedral connected by covalent B—O—B bonds. Species of this sort are expected to be chemically inert and very hard due to strong B—O bonds. However, the polymeric array of dianionic cages is expected to serve as a source of electrons for chemical processes while still retaining water solubility. In addition, the possibilities of the covalent incorporation of species, such as $Cs_2[closo-B_{12}(OH)_{12}]$, in metal oxide lattices are boundless.

Figure 6:
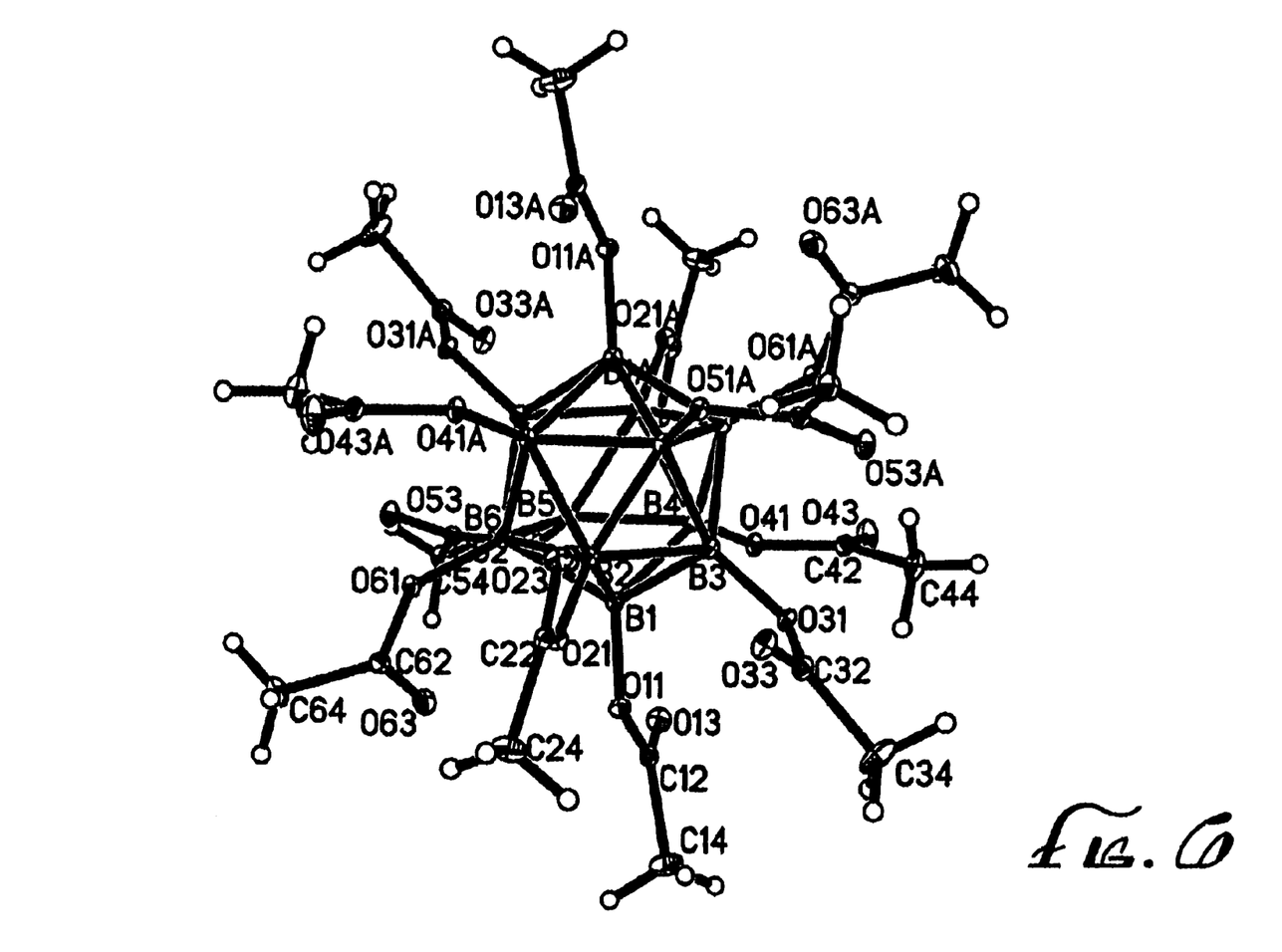
FIG. 6 is an ORTEP diagram of $[closo-B_{12}(OCOCH_3)]^{2-}$.
Figure 7:
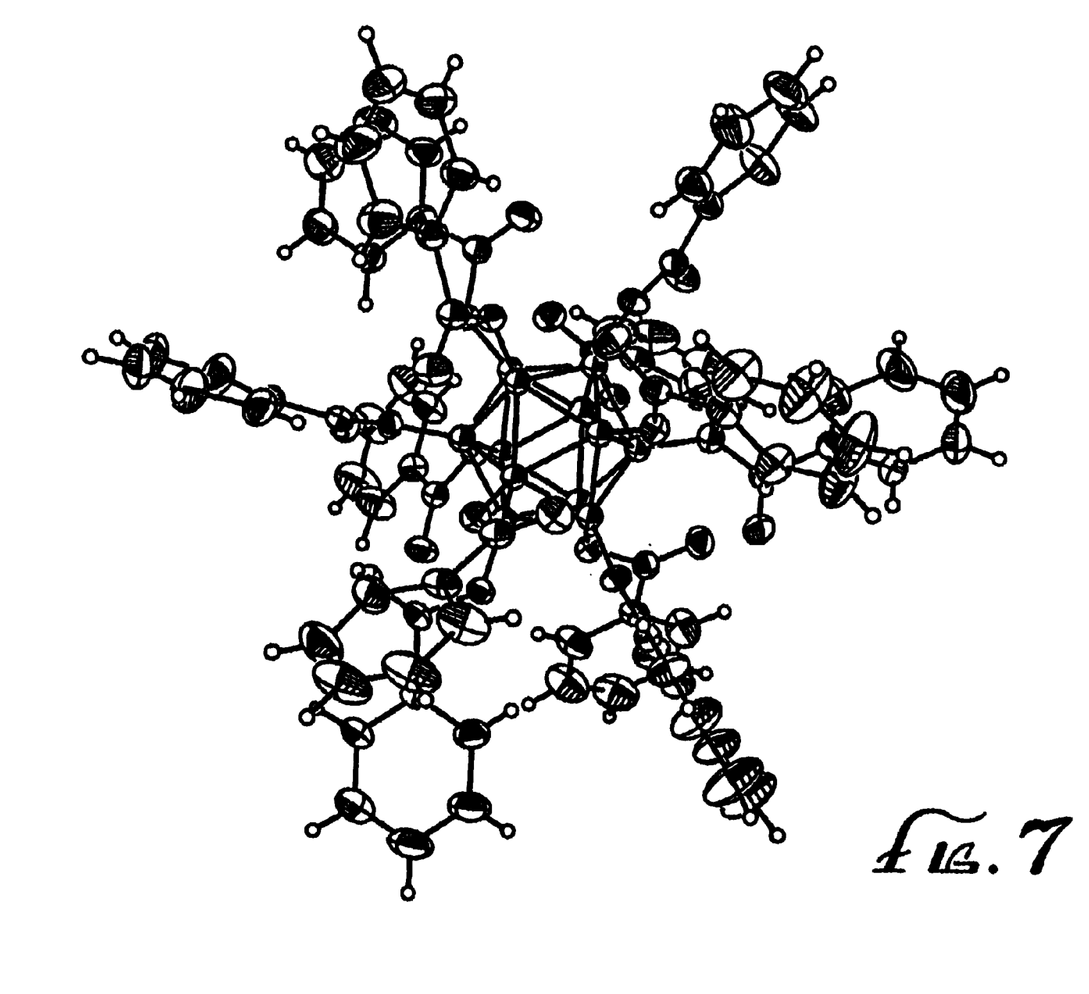
FIG. 7 is an ORTEP diagram of $[closo-B_{12}(OCOPh)]^{2-}$.
Figure 8A:
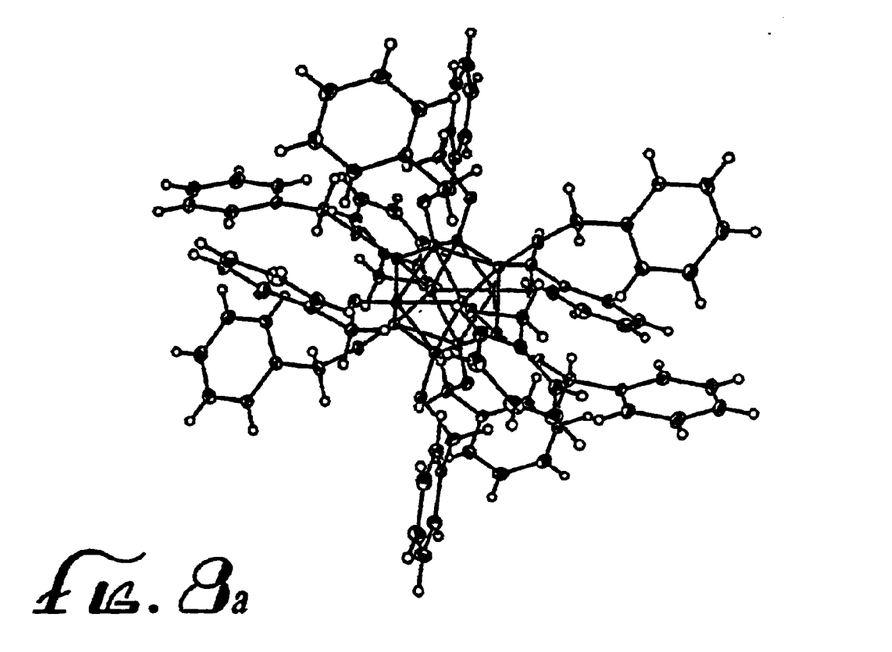
FIG. 8a is an ORTEP diagram of $[closo-B_{12}(OCCH_2Ph)_{12}]^{2-}$
Figure 8B:
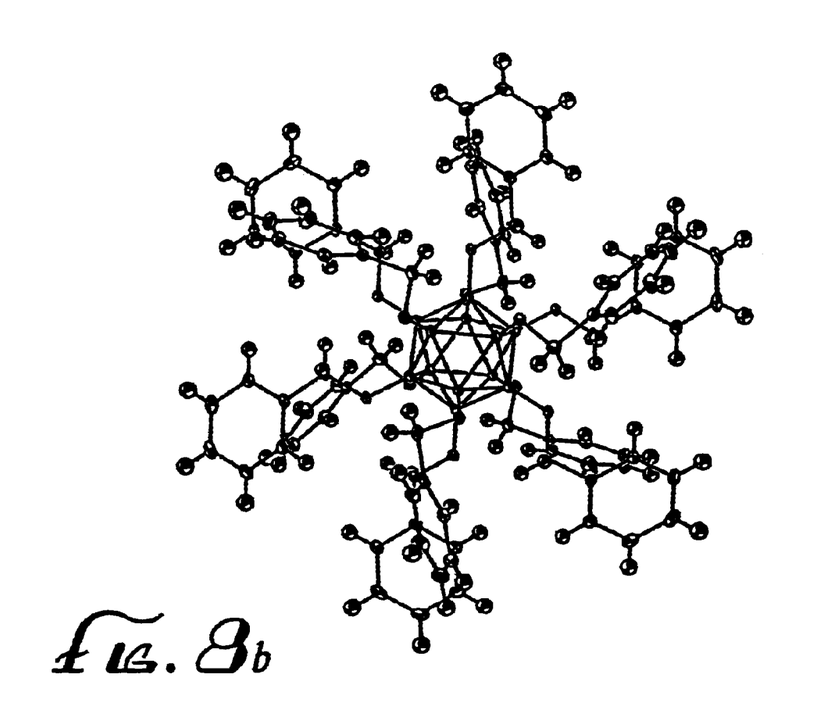
FIG. 8b is an ORTEP diagram of neutral $closo-B_{12}(OCCH_2Ph)_{12}$

It has now been found that dodecahydroxy-closo-dodecaborate(2-) $B_{12}(OH)_{12}^{2-}$ can be reacted with anhydrides and acid chlorides to produce dodecaester derivatives, in which each hydroxy group is converted into an ester function. In a preferred embodiment, the esterification was conducted using acetic acid anhydride, propionic acid anhydride, benzoyl chloride and terephthaloyl chloride. If acid chlorides are employed for the esterfication the presence of a base, such as 2,6-lutidine or triethylamine appears to be necessary. FIG. 6 is an ORTEP diagram of $[closo-B_{12}(OCOCH_3)]^{2-}$. Only the carbon and oxygen atoms are labeled because of the complexity of the structure representation and further identification could clutter the drawing. The central cluster is made up entirely of boron atoms; the open circles on the outer ends of the structure are hydrogen atoms. FIG. 7 is an ORTEP diagram of $[closo-B_{12}(OCOPh)]^{2-}$— For the same reason, none of the atoms are labeled. However, one skilled in the art will readily recognize the identity of each of the atoms based on the description herein.

The use of terephthaloyl chloride allows cross-linking with other carbonyl reactive species, such as amines. This is demonstrated by reaction of $B_{12}(OH)12^{2-}$ with terephtaloyl chloride in 1,2-dichloroethane, followed by the reaction with propylamine. In the resulting product each boron-oxygen moiety is cross linked with propylamine through a terephthaloyl group.

The reaction of $B_{12}(OH)_{12}^{2-}$ with benzyl chloride provides dodecaether derivatives. Also a variety of other similarly reactive halogenated alkylating agents can be used to produce icosahedral ether derivatives using similar reaction conditions. The oxidation of $[B_{12}(OCH_2Ph)_{12}]^{2-}$ with iron (III) in methanol gives a red paramagnetic mono-anion. Further oxidation of this mono-anion with iron(III) leads to an orange, diamagnetic, neutral dodecaether compound. While the cesium salt has limited solubility it was found to sufficient solubility in acetic acid anhydide to initiate the reaction at 120° C. As the reaction proceeded and small amounts of ester were formed the solubility increased and the reaction rate increased, the reaction product being very soluble in the anhydide/acid mixture which was present. It was also found that solubility and reaction rate could be enhanced by utilizing the tetra butyl ammonium slat in place of the cesium salt Of particular significance, it is now possible to form fully subsituted esters and ethers of the dodecaborate, $[B_{12}H_{12}]^{2-}$, and then incorporate the dodecaborate cluster in numerous new compounds using typical reactions of esters and ethers. The total functionalization of the $B_{12}$-icosahedron produces the core of closomers (large chemical structures based on the closopolyhedralborane). These closomers may have branched (dendritic) chains or linear oligomeric chains. The closomeric structures provide camouflaged modules of variable size, shape, charge, hydrophobicity, etc. designed to accomplish a hugh variety of functions. The closomers can find applications in the fields of medicinal chemistry (e.g., in drug delivery systems), host-guest chemistry, catalysis and material science, amongst others.

EXAMPLE 1

Figure 9A:
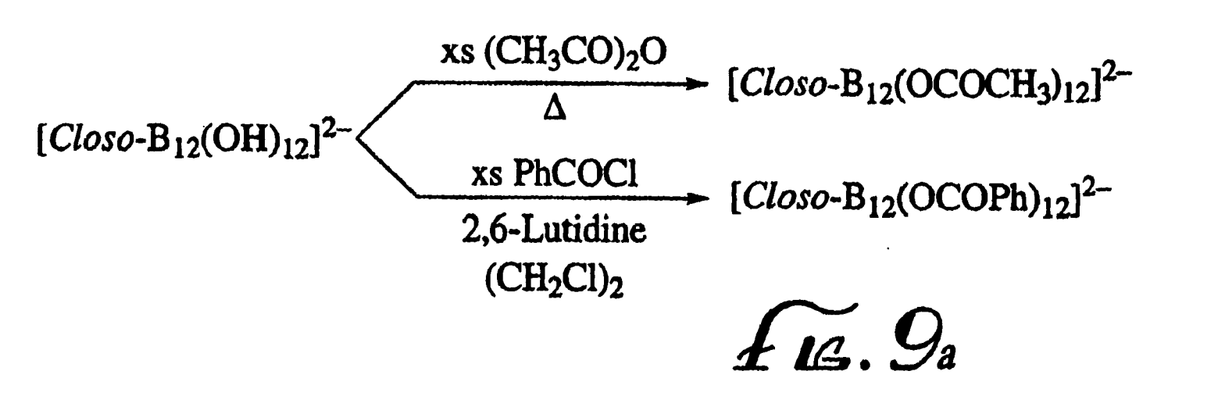
FIG. 9a shows the reaction scheme for formation of an alkyl ester dianion.

Synthetic procedure for $[B_{12}(OCOCH_3)_{12}]^{2-}$: 1 gram of $(Cs_2)$—$[B_{12}(OH)_{12}]$ was suspended in excess acetic acid anhydride (20 ml) and the mixture was heated with stirring to 120° C. for 24 hours. It was then cooled down and the excess acetic acid anhydride and the acetic acid was removed in vacuo. Twenty-five ml (25 ml) of water was added to the residue and the mixture was filtered. The water was then removed in vacuo, leaving 1.61 g of $(CS_2)[B_{12}(OCOCH_3)_{12}]$ for a yield of 87% yield. (See FIG. 9a). FIG. 9a also shows a similar reaction using benzoyl chloride.

EXAMPLE 2

Synthetic procedure for $[B_{12}(OCOPh)_{12}]^{2-}$: Three hundred milligrams (300 mg) of $(NBu_4)_2$-$[B_{12}OH_{12}]$ was dissolved in 25 ml of dry 1,2-dichloroethane. 10 ml of triethylamine and 5.5 ml benzoyl chloride were added to this solution and the solution was heated to 120° C. with stirring for 5 days. The dark colored reaction mixture was cooled down and the solvent removed in vacuo. The residue was washed 2 times with hot toluene and then dissolved in hot acetonitrile and filtered. To the dark-colored filtrate was added the same volume of water, resulting, in the formation of a dark oily precipitate. This oily precipitate was then separated and dried in vacuo for 8 hours. The brown solid which remained was purified by flash chromatography using silica as the stationary phase and acetonitrile as the mobile phase to produce 476 mg pure $(NEt_3)_2$-$[B_{12}(OCOPh)_{12}]$ for a yield of 72%. Single crystals for X-Ray analysis were obtained by substitution of the triethylammonium cations with PPN cations in a mixture of DMF, $H_2O$ and EtOH.

EXAMPLE 3

Figure 9B:
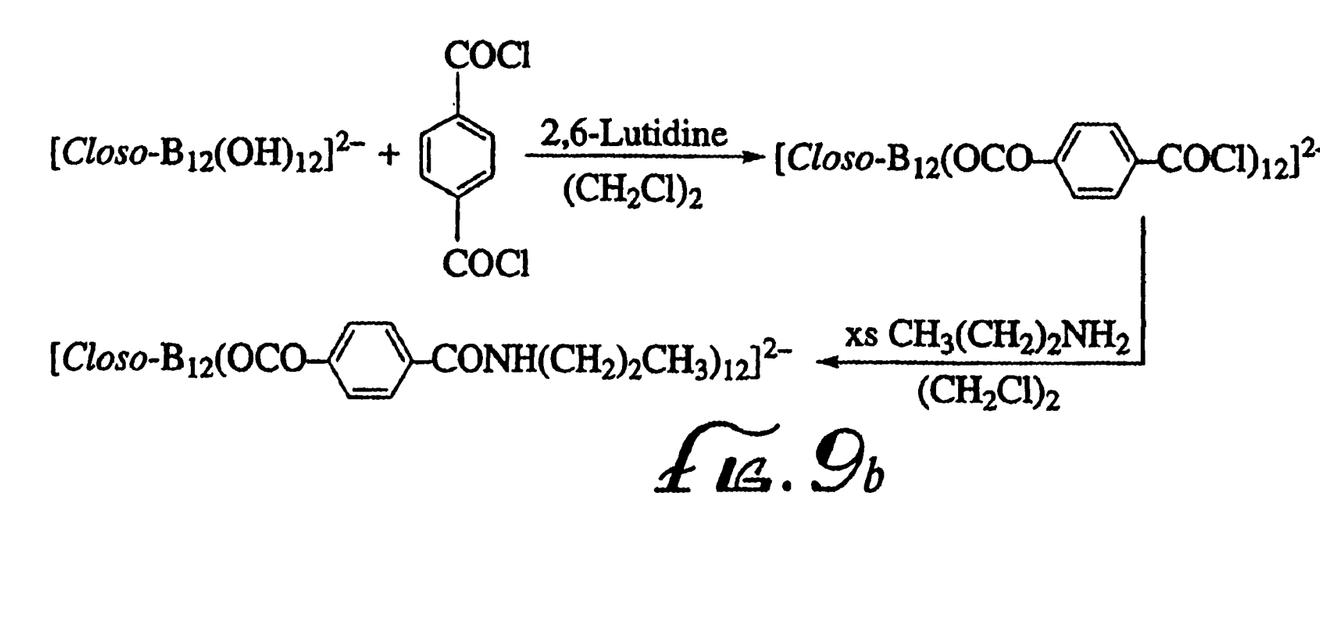
FIG. 9b shows the reaction scheme for formation of a phenyl ester dianion.

Synthetic procedure for $[B_{12}(OCO-C_6H_4-CONHC_3H_7]^{2-}$: Two hundred and ten milligrams (210 mg) of $(NBu_4)_2$—$[B_{12}(OH)_{12}]$ was dissolved in 40 ml of dry 1,2-dichloroethane. Twelve milliliters (12 ml) of triethylamine and 6.334 g terephthaloyl chloride were added to this solution and the resultant suspension was heated at 120° C. with stirring for 5 days. A dry residue resulted when the mixture was cooled down and the solvent removed in vacuo. An excess of propylamine (30 ml) was slowly added to the dry residue and the mixture was stirred for 2 days. The addition must be done carefully as the reaction is exothermic. Subsequent removal of excessive propylamine gave a brown residue which was then washed with toluene and diethyl ether, dissolved in hot acetonitrile and filtered. The same volume of water was added to the filtrate. At the end of 10 hours a brown precipitate was present. The precipitate was washed 2 times with toluene and purified with chromatography (silica, acetonitrile) to give 414 mg product (69% yield). (See FIG. 9b)

Figure 10A:
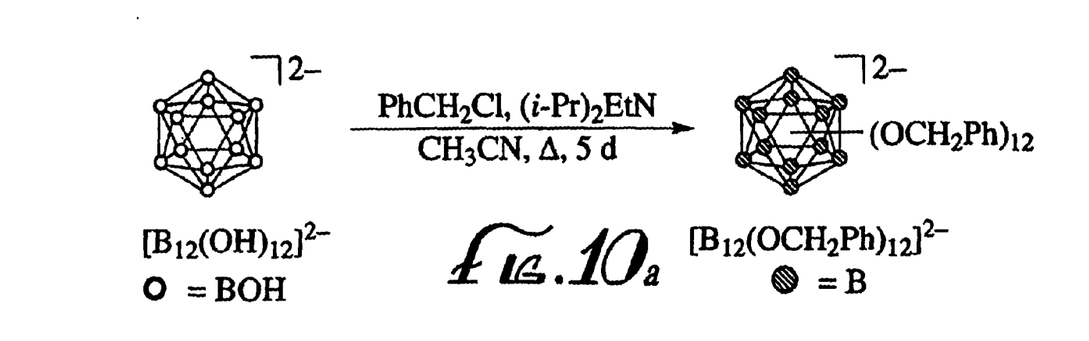
FIG. 10a shows the reaction scheme for formation of a phenyl ether dianion.
Figure 10B:
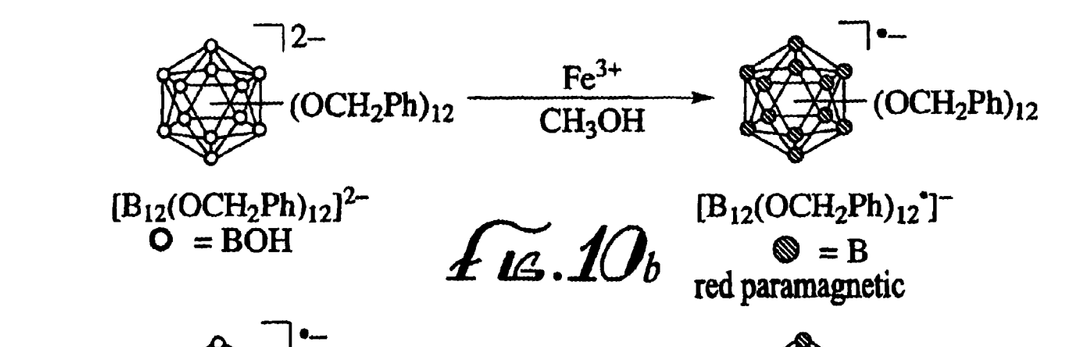
FIG. 10b shows the reaction scheme for formation of a paramagnetic phenyl ether anion.

EXAMPLE 4 (See FIG. 10a, and 10b)

Synthetic procedure for $B_{12}(OPh)_{12}$:

A quantity of $(PPN)_2$—$[B_{12}(OH)_{12}]$ (0.60 g) was dissolved in acetonitrile (10 ml) and 0.88 ml of Hunigs base to which 5.7 ml of benzyl chloride was added. The reaction mixture was heated at the reflux temperature for 3 days. The volatiles were removed in vacuo and the residue twice mixed with 50 ml of pentane, the pentane being discarded. To the residue, 20 ml of 95% ethanol was added and the solid filtered off. Sodium borohydride was added to the filtrate until the mixture turned colorless. The precipitate obtained was filtered off and dried to yield 400 mg of [PPN]Na—$[B_{12}(OPh)_{12}]$ (FIG. 10a).

A quantity of the [PPN]Na—$[B_{12}(OPh)_{12}]$ (0.12 g) was then dissolved in ethanol (10 ml) and 0.05 g of $FeCl_3.6H_2O$ was added. The reaction mixture was filtered and the resultant solid was dissolved in acetonitrile and again filtered. The acetonitrile was removed and the residue recrystallized from ethanol to give 0.06 g [PPN]—$[B_{12}(OPh)_{12}]$, a red paramagnetic monoanion (FIG. 10b).

Figure 10C:
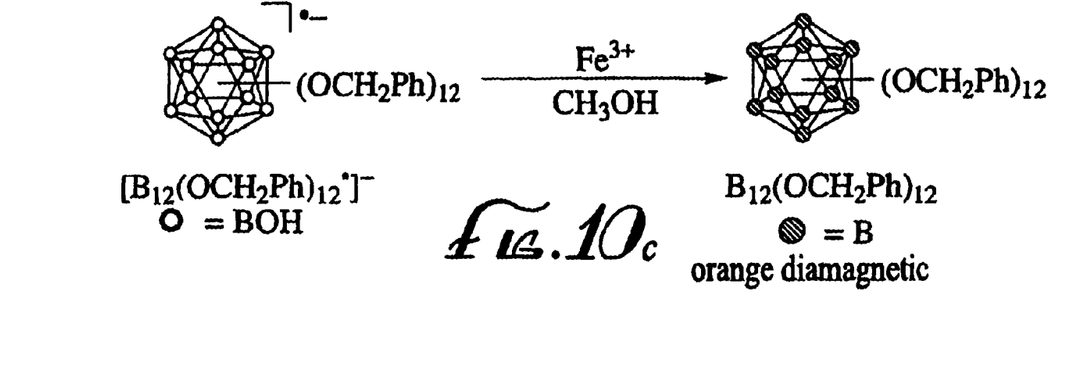
FIG. 10c shows the reaction scheme for formation of a neutral, diamagnetic phenyl ether.

EXAMPLE 5 (See FIGS. 10a, 10b and 10c)

A quantity of $K_2$—$[B_{12}(OPh)_{12}]$ (0.100 g) was dissolved in ethanol (10 ml) and two equivalents of $FeCl_3.6H_2O$ were added. The reaction mixture was filtered and the obtained solid recrystallized from acetonitrile to give 0.06 g of $B_{12}(OPh)_{12}$.

It is evident from the foregoing that there are many additional embodiments of the present invention which, while not expressly described herein, are within the scope of this invention and may suggest themselves to one of ordinary skill in the art. For example, while acetic acid anhydride, propionic acid anhydride, benzoyl chloride and terephthaloyl chloride have been used, it is contemplated that a broad range of acid anhydrides, and acid chlorides can be used including, but not limited to (α-bromo-aceticacid anhydride. While examples show reactions of $B_{12}$; cosahedrons, it is believed the same reaction schemes can be utilized to produce ethers and esters of $B_{10}$ and $B_{11}$ cage compounds. Also various different halogenated alkanes or cyclic acids can be used in place of benzoyl chloride, such as terephthaloyl chloride and other halogenate daromatic compounds. Still further, it. is contemplated that the process is can be used to produce ether and esters of alkenes and alkynes as well as alkanes (i.e. ethers and esters which include double (=) and triple (≡) bonds and the phenyl can have a broad range of substituents appended thereto. One skilled in the art, in light of the teachings herein, will recognize the extensive range of reactants which can be used to form ethers and esters and substituted ethers and esters. Also, once the esters are formed, one skilled in the art will recognize that a broad range of compounds can be formed from the esters and ethers. For example, the further reaction with amines is discussed. It is therefore intended that the invention be limited solely by the appended claims.

We claim:

1. A three-dimensional icosahedral ester boron cage compound wherein at least ten of the icosahedral cage compound vertices comprise boron atoms, and the other two icosahedral cage compound vertices comprise either a boron atom or a carbon atom, each boron atom having an ester group attached thereto.

2. [closo-$B_{12}(OCOR)_{12}]^{2-}$ where R is alkyl, alkene or alkyne or a phenyl group.

3. A method of preparing a three dimensional icosahedral cage compound, the twelve vertices of the icosahedral cage compound comprising boron atoms, each boron atom having an ester group attached thereto, comprising:

a) reacting dodecahydroxy-closo-dodecaborate with an excess of anhydride or and acid chloride with heating and stirring for a period of time sufficient to complete the reaction, b) removing unreacted anhydrides or acid chloride to leave a residue, c) washing the residue with water and filtering the mixture to separate all undissolved material from the filtrate, d) removing the water from the filtrate and e) collecting the three dimensional icosahedral ester boron cage compound which remains.

4. The process of claim 3 wherein the anhydride is acetic acid anhydride, the heating temperature is at least about 120° C. and the time is at least about 24 hours.

5. A method of preparing a three dimensional icosahedral cage compound, wherein ten vertices of the icosahedral cage compound comprise boron atoms, and the other two vertices of the icosahedral cage compounds comprise boron or carbon atoms, each boron atom having an ester group attached thereto, comprising:
   a) reacting a three dimensional icosahedral cage compound, wherein ten vertices of the icosahedral cage compound comprise boron atoms, and the other two vertices of the icosahedral cage compounds comprise boron or carbon atoms, each boron atom having a hydroxyl group attached thereto, with an excess of anhydride or and acid chloride with heating and stirring for a period of time sufficient to complete the reaction,
   b) removing unreacted anhydrides or acid chloride to leave a residue,
   c) washing the residue with water and filtering the mixture to separate all undissolved material from the filtrate,
   d) removing the water from the filtrate and
   e) collecting the three dimensional icosahedral ester boron cage compound which remains.

* * * * *